(12) United States Patent
Gullett et al.

(10) Patent No.: US 8,062,610 B2
(45) Date of Patent: Nov. 22, 2011

(54) APPARATUS AND METHODS FOR USE IN CONCENTRATION OF GAS AND PARTICLE-LADEN GAS FLOWS

(75) Inventors: Brian K. Gullett, Durham, NC (US); Abderrahamne Touati, Raleigh, NC (US); Shawn Ryan, Durham, NC (US); William Squier, Angier, NC (US)

(73) Assignee: The United States of America as represented by Environmental Protection Agency, Washington, DC (US)

(*) Notice: Subject to any disclaimer, the term of this patent is extended or adjusted under 35 U.S.C. 154(b) by 1326 days.

(21) Appl. No.: 11/355,189

(22) Filed: Feb. 16, 2006

(65) Prior Publication Data

US 2006/0258017 A1 Nov. 16, 2006

Related U.S. Application Data

(60) Provisional application No. 60/681,146, filed on May 16, 2005.

(51) Int. Cl.
*G01N 1/10* (2006.01)
(52) U.S. Cl. .......... 422/534; 422/89; 422/616; 422/267; 210/107; 210/145; 95/113; 96/191; 96/192; 55/285; 261/83

(58) Field of Classification Search ................ 73/19.02, 73/23.35–23.42, 61.56; 210/659, 107, 216, 210/323.1, 145; 422/89, 534, 616, 267; 95/89, 95/113, 277; 96/105, 189–192, 219, 233, 96/240, 241, 124, 125; 55/285, 350.1, 447; 165/110; 34/480; 261/83
See application file for complete search history.

(56) References Cited

U.S. PATENT DOCUMENTS

| | | | | |
|---|---|---|---|---|
| 2,080,578 A * | 5/1937 | Ray | ................................ | 96/130 |
| 3,891,417 A * | 6/1975 | Wade | ......................... | 96/117.5 |
| 4,054,417 A * | 10/1977 | Rosebrock | ..................... | 422/171 |
| 5,288,310 A * | 2/1994 | Peters et al. | ..................... | 96/104 |
| 6,457,485 B2 * | 10/2002 | Hill et al. | ....................... | 137/240 |
| 6,905,534 B2 * | 6/2005 | Chang et al. | ...................... | 96/55 |
| 2006/0113231 A1 * | 6/2006 | Malik | ........................ | 210/198.2 |

* cited by examiner

*Primary Examiner* — Brian R Gordon
*Assistant Examiner* — Shogo Sasaki
(74) *Attorney, Agent, or Firm* — Glenna Hendricks; Hendricks & Assoc.

(57) ABSTRACT

For analysis of small quatities of target analytes in an environment, the gas flow can be delivered to a suitably fast analyzer and their concentration determined in a time period whose duration is dependent on the analyte, its concentration and the phase separation properties. A device having a sorbent bed that is essentially concentric with a passage way containing thermal fluid is used to concentrate the target analyte.

12 Claims, 6 Drawing Sheets

APPARATUS AND METHODS FOR USE IN CONCENTRATION OF GAS AND PARTICLE-LADEN GAS FLOWS

This application takes priority from Provisional Patent Application 60/681,146 filed May 16, 2005.

FIELD AND BACKGROUND OF THE INVENTION

The present invention relates to an apparatus for sampling particle-laden gas flows and concentrating trace organic species within that flow for subsequent analysis by gas phase detectors.

Environmental sampling for target chemical species often requires knowledge of gas/particle phase partitioning. The partitioning of target chemicals such as pollutants between the gas phase atmosphere and the surfaces of particles has implications in study and analysis of transport model predictions, atmospheric reaction modeling, and evaluation of pollutant formation/evolution mechanisms. The actual partitioning of these target chemical species between gas phase and condensation/absorbed solid phase as a function of their vapor pressure, concentration and solubility are important aspects in such studies. System temperature and characteristics of the absorptive particle surfaces are also important factors in partitioning. Sampling methods to determine the concentration and/or partitioning of the target chemicals can affect the actual partitioning. Sampling systems which operate with a particle filter allow accumulation of particulate solids during the sampling episode, which may last over 3 hours. These particles can act as sorptive surfaces for gas phase targets through condensation or absorption/reaction phenomenon ("blow-on"), thereby transferring the target analytes to the solid phase. (See, for example, articles by Cotham & Bidleman in *Eniron. Sci. Tech.* 24, p 342 and Gundel, et al., *Atmos. Environ.* 29, p. 1795 (1995).) Alternatively, the filter surfaces can lose particle-bound volatile target analytes to the downstream collection media ("blow-off"), thereby biasing results toward gas phase partitions as described by Eatough, et al., (*Organic Chemistry of the Atmosphere* CRC Press, 1999). These sampling artifacts introduce bias into determinations of phase partitioning of volatile and semi-volatile compounds.

For analysis of target species, concentration methods are often employed to bring the quantity of target above the analytical detection limit of the apparatus. This includes methods such as cryogenic focusing, pressure swing absorption as described by Keefer in U.S. Pat. No. 4,968,329, which is incorporated herein by reference, and sorbent collection as described by Sides, et al., in U.S. Pat. No. 5,014,541 and Pleil, et al., U.S. Pat. No. 5,447,556 (extraction/solvent evaporation), both of which are hereby incorporated by reference. These methods teach gas phase target concentration, but do not address maintaining and preserving the distinction in the trace organic species phase (vapor or condensed on particles) as exists at the point of sampling.

There are some sampling methods that address phase partitioning of targets. The standard EPA (Environmental Protection Agency) method train (U.S. EPA, Test Method 0032A) consists of a filter housing through which the particle-laden gas stream passes followed by an absorbent media. This method can provide a gas versus particle phase distribution, but can suffer considerable bias from the blow-off and blow-on phenomena discussed above, and, hence, is not purported as a method for discerning analyte phase partitioning. As an alternative, denuder sampling has been developed in an effort to continually separate gas phase targets from the solid phase targets. Annular denuders consist of one or more channels through which both gasses and particles pass. The denuder surfaces may be coated with a thin layer of fine absorbent. The denuder principle relies on the relatively faster diffusion of the gas phase target to the denuder wall than that of the exposure of particles to the wall in this laminar flow regime. In this manner, the gas phase components are separated from the particle stream. In most denuder applications, the particle stream is filtered and followed by a sorbent that catches target analyte blow-off. The denuder surface can be solvent-extracted and analyzed for the target components in the vapor phase or vapor phase components can be determined simply by the difference of the post-denuder filter catch and a separate total sample catch. Bias in denuder operations results from fine particle diffusion to denuder walls (estimated at 10% for 0.1-0.05 m particles), volatilization of target analytes from particles during transit through the denuder channels, and breakthrough of the volatiles from the denuder to the downstream adsorbent.

A method of particle segregation of gas streams is taught to create a particle-free stream and a particle-rich stream in a method (U.S. Pat. No. 5,746,789 to Wright and Crouch, which is incorporated herein by reference). That method of segregation increases the relative gas to particle velocity, thus exacerbating concerns over particle blow-off and blow-on.

Many filters have been taught as providing means for avoiding pressure drop caused by the buildup of particles of simply as means of particle filtration. Some moving filters include self-cleaning processes (U.S. Pat. No. 5,560,835). The references show intent only to limit pressure drop due to particle buildup on the filter. None of the references teach a method for limiting gas flow through previously filtered particles, thereby minimizing blow-off and blow-on complications.

SUMMARY OF THE INVENTION

This invention provides a gas/particle sampling method for separation and concentration of volatile and/or semi-volatile gas/vapor analytes that are present in dilute concentrations in a gas stream phase or as a condensed phase on particles within the stream. The target analytes can be delivered in gaseous form to a suitably fast analyzer and their concentration determined in a time period whose duration is dependent on the analyte, its concentration and the phase separation properties. A key feature of the method is its ability to preserve the analyte's gas/particle partitioning by minimizing adsorption or desorption of analytes onto the particle-laden filtering surface. One aspect of the invention is the use of a filter having continually refreshed surfaces. The filter exemplified has rotating filters which can be repeatedly refreshed. However, a filtering tape can also provide means of providing fresh surfaces to collect particles.

The device for use in the practice of the invention comprises at least one sorbent bed through which is passed a gas supposed to contain a target analyte. The bed is essentially concentric with a passage way containing thermal fluid such as a tube which may either surround the sorbent bed (see FIG. 2) or the sorbent bed may surround the passage way (FIG. 5). The thermal fluid passage way is accessed through an entrance port and an exit port which allows a heat transfer thermal fluid to flow into and out of the passage way. After passage through one or more sorbent beds, the gas may be passed through a cryotrap to significantly shorten the time duration in which the target analytes are released from the system to the analyzer. (Concentric, in this specification, represents passages which would be orientated around a common center point on a line passed through a cross section of the concentrator.)

The methods of the invention provide for concentrating target gas analytes into a small volume gas sample while minimizing blow-off and blow-on of the target gas analytes through a filtration system which, separate or in combination, provide a particle-free, concentrated gas stream containing the sample of gas-phase target analyte which can then be sent to an appropriate end processor, such as an analytical gas monitor. Particles are removed by a filtration apparatus which has multiple filters, allowing for incremental refreshment of the filter surface to minimize the exposure time of the captured particles to the flowing gas, thereby minimizing blow-off and blow-on. Volatile and semi-volatile target gases are removed from a flowing gas stream by diffusion and/or adsorption to a cold sorbent resin bed.

Sequential differential heating/cooling regimes are used to concentrate the target gases in a small gas volume for subsequent use or analysis. This eliminates large gas volumes associated with separation of typical volatile solvents. After a sampling time sufficient to reach the detection limits of the back end instrumentation for the target analyte, the inflow is stopped. The target species is then concentrated and removed from the sorbent resin bed by rapid heating to a temperature that is a function of the desired species vaporization properties by desorbing at a flowrate less than the sampling flow rate. Alternatively, or in combination, a pre-concentrator filter can be heated to a species-dependent temperature to volatilize all particle-bound target species, which then delivers these species to the concentrator for subsequent concentration as required. Briefly, the steps of the invention comprises a method of concentrating and identifying a target analyte from a gas or vapor comprising the steps of: a) passing a gas or vapor through a filter to remove particulate matter through a valve into a gas/vapor concentrator having at least one sorbent bed in a gas/vapor passage which may be comprised of at least one of sorbent surfaces and packed sorbent resins which will adsorb the target gas, said gas/vapor passage having a sorbent bed being concentric with an imbedded or a surrounding passage containing heat transfer fluid, b) adjusting the temperature of the sorbent bed to the condensation temperature of the target analyte to permit adsorption of the target analyte, c) allowing escape of the gas essentially free of the target analyte to exit the concentrator system, then d) admitting into said passage having a sorbent bed an inert carrier gas while raising the temperature of the said bed to a temperature sufficient to cause desorption of the target analyte, then, e) discharging the gas containing the target analyte and the carrier gas into a measuring device. The carrier gas with the analyte may be passed through a cryotrap to condense gas further before release of gas to the detection device. However, it is also possible to pass the carrier gas containing the analyte obtained in step d directly into the measuring device without passage through a cryotrap.

The apparatus comprises in series, a filter tray comprised of multiple filter holders, each containing a filter, a first inlet valve which, when open, transmits a gas or vapor into a concentrator system composed of at least one gas/vapor passage having a sorbent bed concentric with a passage containing thermal heat transfer fluid, an exit valve from which gas can escape, a second inlet valve through which a carrier gas passes and a second outlet valve through which gas is passed the detection device, optionally through a cryotrap, into the detection device.

DETAILED DESCRIPTION OF THE INVENTION

Figure 1:
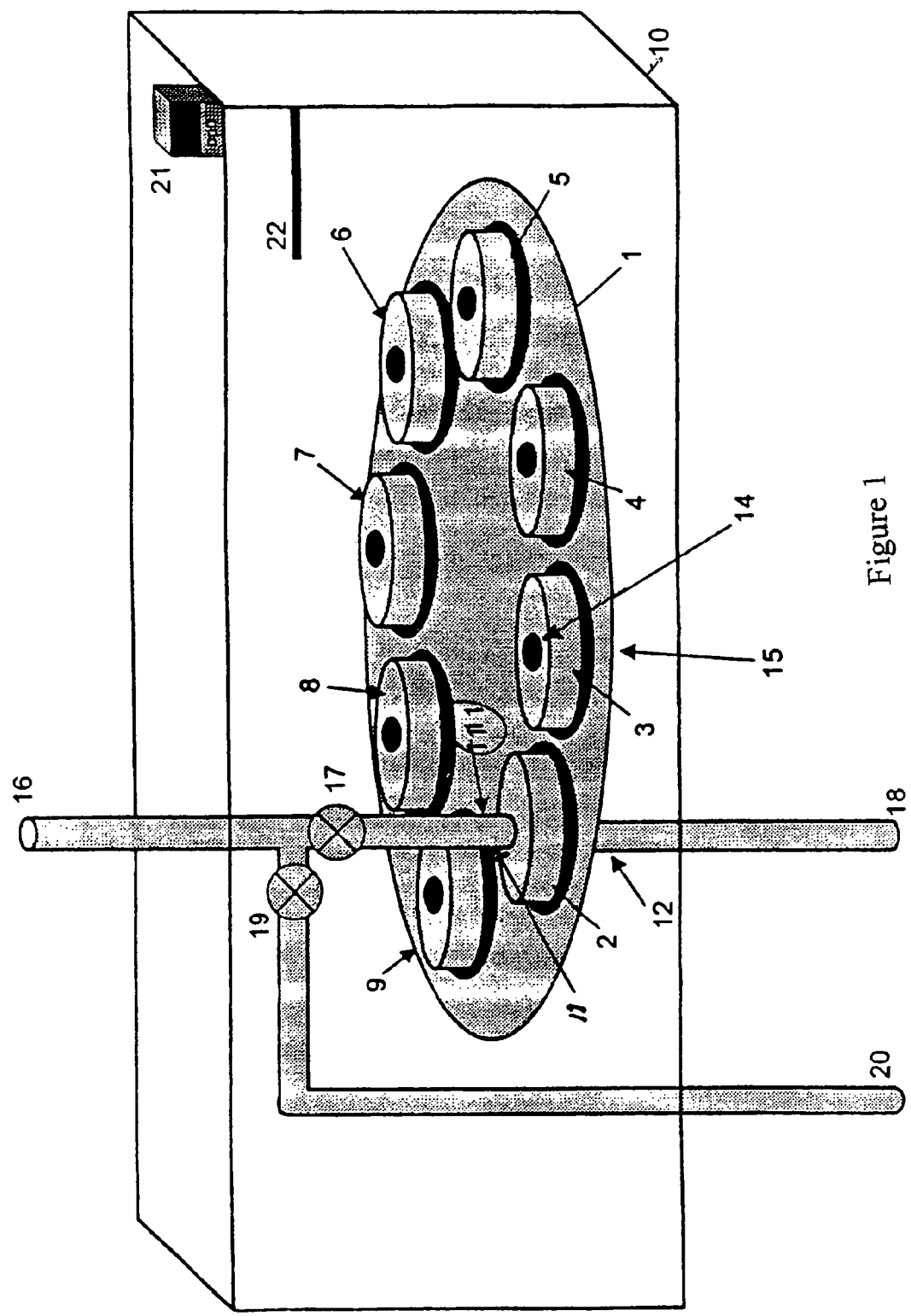
FIG. 1 is a perspective side view of a filter system for removing particles, if any, from the gas flow.

It is a purpose of this invention to provide an apparatus and methods for operation of said apparatus for sampling gases containing trace organic species, both in the vapor phase and as condensed on particles, and to concentrate the target trace organic species. Means for surpassing analytical detection method limits of a gas analyzer prior to passing the collected sample containing the target analyte to the analyzer are also taught herein. It is also the purpose of the invention to provide means for distinguishing between the trace organic species that are in the vapor phase from those which were bound to the particulate phase in such a manner that there is no alteration that would prevent such distinction. Using methods of the invention it is possible to make such a distinguishing analysis without passing the particles, to which the target species may be bound, to the analyzer. This is important, since many analyzers can not tolerate the presence of such particles.

This invention, like a denuder, removes the gas phase target analyte from the gas stream. However, use of solvent rinses is not required. The method of the invention applies different heating regimes to concentrate the target gases in a small gas volume for subsequent use or analysis. This eliminates the large volume associated with separation of the volatile solvent. Kawakami, et al., in U.S. Pat. No. 6,165,254, which is incorporated herein by reference, teaches use of absorption/desorption via heating in a gas concentration device containing absorption and desorption zones followed by passage through a cooling zone comprising a rotating honeycomb rotor. However, that reference does not address the presence of solid particles nor the removal and concentration of gases condensed on the particles. This issue is addressed by the present invention.

A preferred embodiment of the invention is shown in the drawings. However, other apparatus with equivalent function are appropriate for practice of the invention and, therefore, may also be used in practice of the invention.

The sampling of gas-phase volatile and semi-volatile organic compounds from a particle-laden gas stream with target compounds concentrated in a carrier gas to provide a particle-free sample is carried out as described below. Minimal target loss via adsorption onto the filter occurs, allowing for an accurate measure of the gas phase fraction. A concentrator was designed which operates on the principal of trapping the target compounds by absorbing them from an exhaust gas on the cooled sorbent resin bed of a zone concentrator system. A sequential cooling and heating process causes the target compounds to be moved and concentrated with reduction of the carrier gas volume. The concentrated organic target can then be conveyed to a suitable detector. The following flow-chart is provided as a guide to factors considered in fashioning the system of the invention. The use of more than one resin bed concentrator unit, there is step-wise reduction in the volume.

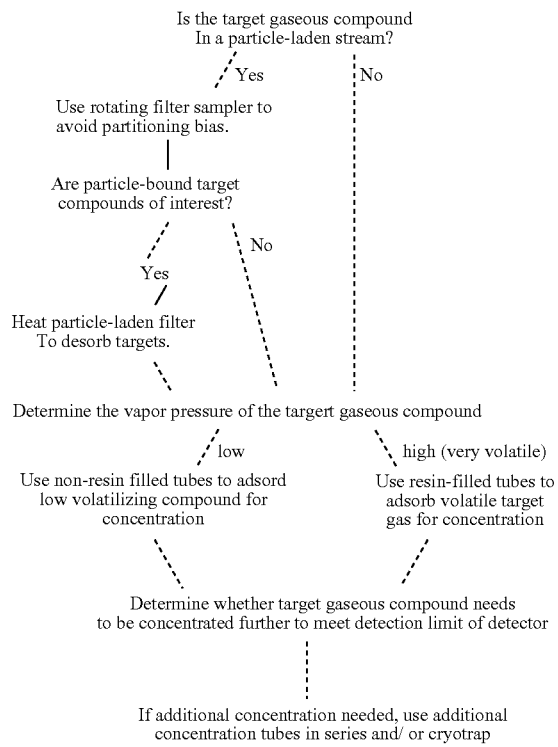

Additional concentration after passage through the last concentration tube(s) may be achieved by passing the output of the concentrator system and, optionally, through a cryotrap before passage to the detection device, with the proviso that passage through a cryotrap is not always required.

The combination of the filter with a thermal system disclosed herein allows for the sampling of gas that has semi-volatile organic compounds from a particle-laden gas stream producing a particle free stream with the target compounds concentrated in an inert carrier gas. Minimal target loss via absorption onto the filter occurs allowing for an accurate measurement of the gas phase concentration of the target compounds by any of a variety of downstream detectors. It should be noted that the choice of different sensitive downstream detectors depending on the target gas from those exemplified is entirely appropriate and within the scope of this invention.

Referring to the figures, FIG. 1 shows a filter tray 1 containing eight filter holders 2-9 enclosed in an oven 10. The filter tray is motorized and precision-controlled via limit switches in order to place the desired filter contained in each filter holder 2-9 into position between the inlet line 11 and the outlet sample line 12. Once the desired filter is in place, the inlet 11 and outlet 12 sample lines are sealed to the filter inlet 14 and outlet 15 (obscured) openings with a compressed air-driven mechanism. Sampled gas flows in through the filter system inlets 16, through the open valve 17, through the filters 2-9 and out through the filter system outlets 18. After the desired sampling time, valve 17 is closed and valve 19 is opened to allow flow to pass through the bypass line 20. The filter tray 1 is released from its compression between the inlet 11 and outlet 12 sample lines. The tray moves clockwise to rotate the next desired filter 2-9 into place between the inlet and outlet sample lines. The desired sampling time may be manually controlled or controlled via automatic sensors, such as a differential pressure sensor located between the lines 11 and 12. The oven 10 housing the system is controlled by temperature controller 21 with temperature determined via a thermocouple. All filter system actions, with exception of the oven temperature, were controlled by a visual basic computer code capable of manual or automatic (programmed) filter operation. There are many choices in software programs that can be used. The software sold under the name "Visual Basic" was actually used in the methods exemplified herein. The method of controlling the sampling need not, however, be computer controlled, though such is exemplified herein.

After passage of the gas thought to contain the target analyte has been passed through the filter, if it is believed the target analyte has been adsorbed onto the surface of the particles the filters may be heated and the heated gas may then be sent through outlets 18 to the concentrator system for concentration and analysis.

Figure 2:
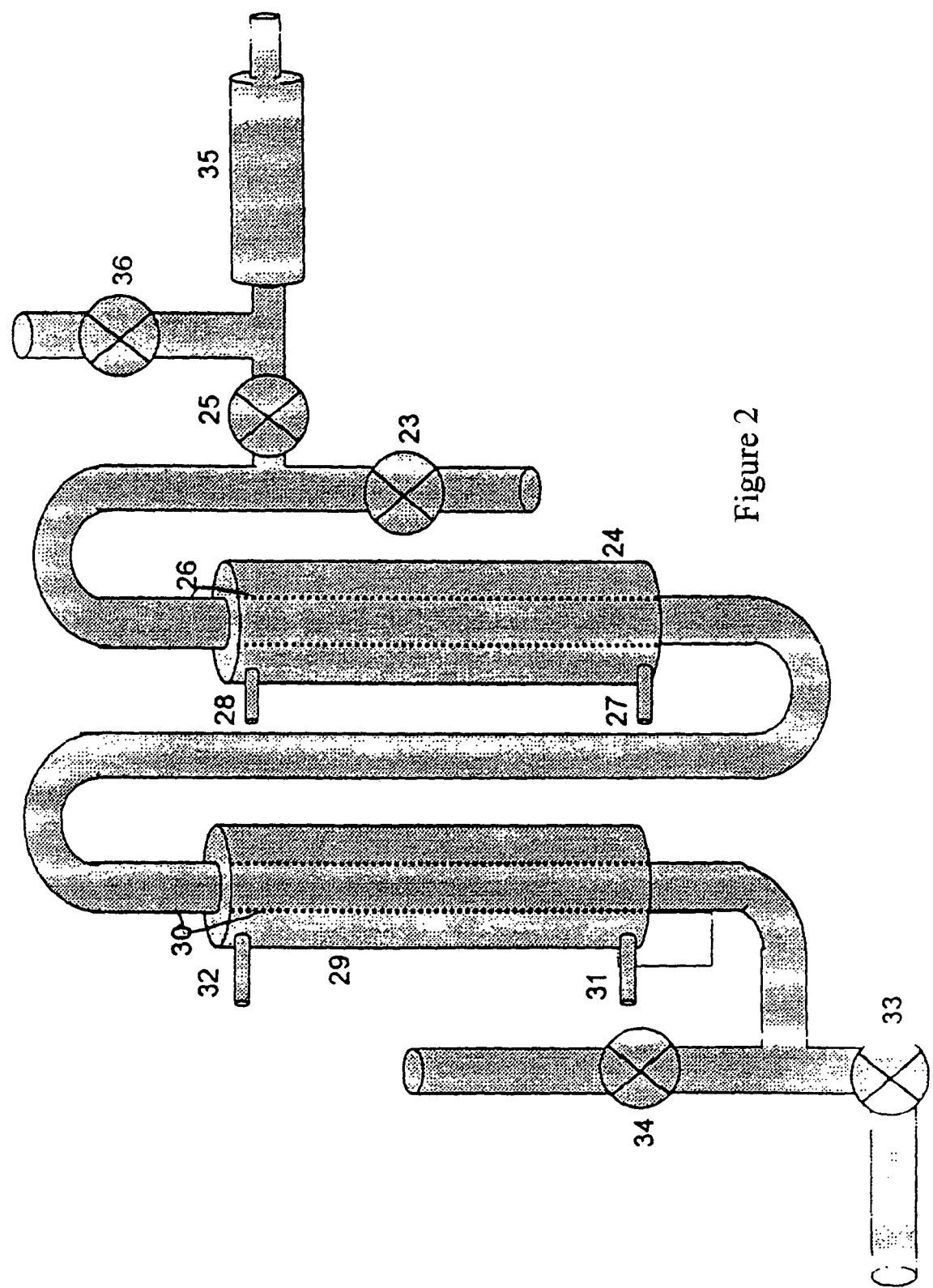
FIG. 2 is a side view of the invention showing sequenced chambers as well as a flow diagram for a thermal control system that envelopes the chambers and a filter system.

Referring to FIG. 2, particles which are contained within the sample gas are retained on the filters in the filter holders 2-9 before the gas is passed on to the concentrator system shown in FIG. 2. The particle-free sample flow at the exit to the filter system 18 enters the concentrator system through an open sample inlet valve 23 and into the hollow tube 26 and exits through the open exit valve with delivery valve 25 in the closed position. The concentrator exemplified in this model has concentrator unit 24. This concentrator section has consists of two concentric cylindrical tubes with the inner tube 26 wrapped with resistive heating elements to rapidly heat the inner tube. In a space between the inner tube 26 and the outer wall of concentrator unit 24, a cooling liquid can be passed in through an inlet port 27 and out through an exit port 28 in order to rapidly cool the inner tube 26 when the heating elements are deactivated. The gas then passes to the sorbent bed of the second concentrator unit having sorbent bed 29 is essentially a duplicate of the first concentrator unit with concentrator 24 except that the tube 30 is filled with a resin-based sorbent. Heat transfer thermal fluid enters the space of the concentrator sorbent bed 29 through an entrance port 31 and exits through an outlet port 32 when the resistive heating elements around the inner tube 30 are deactivated during the absorption phase of the system operation. When gas enters the inner tube 26 of the concentrator 24 with the heat transfer thermal fluid maintaining the tube at the desired condensation temperature (absorption phase), the high boiling point, low vapor pressure semi-volatile target organic compounds contained with the sampled gas stream will be retained on the tube walls. The gas stream is then passed to the inner tube 30 of a second condenser unit which is also kept at a cool temperature by passing a heat transfer thermal fluid through the outer wall of the concentrator, where the more volatile organic compounds are trapped on the resin-based sorbent. The target-free gas stream exits the concentrator system via an open exhaust valve 33 with inert carrier gas valve 34 in closed position. After the desired sampling time, the sample inlet valve 23 and exhaust valve 33 are closed simultaneously with the opening of the inert carrier gas valve 34 and delivery valve 25. Tubes 26 and 30 are then heated to the necessary vaporization or desorption temperature for the target compounds of interest by stopping the heat transfer thermal fluid flow and engaging the resistive heating elements. At the necessary temperatures, the target compounds are added to the inert carrier gas flow via desorption from the resin bed contained in tube 30 and vaporized from the wall of tube 26. After passing through delivery valve 25 target compounds are condensed/adsorbed from the inert carrier gas flow onto the cold walls of the cryotrap 35 with the cryotrap flow valve 36 closed. After the required desorption time, the inert carrier gas valve 34 and delivery valve 25 are closed simultaneously and a very low flow is passed through the cryotrap via cryotrap flow valve 36. The cryotrap 35 is rapidly heated to the delivery temperature and the flow containing the target analytes is passed onto the detection instrument. All actions of the concentrator system shown in FIG. 2 and discussed herein were automated via visual basic computer code allowing for users to adjust parameters such as the absorption and desorption stage temperature and time settings. The temperatures and times entered manually by the user are based on the knowledge of the users, who would be of ordinary skill in the chemical arts relating to the target analytes.

Figure 6:
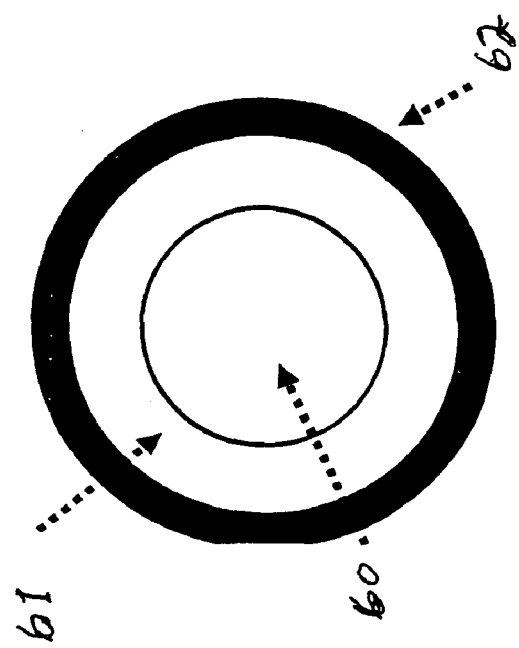
FIG. 6 shows a cross-section view of the adsorption chambers of FIG. 2.

FIG. 6 shows a cross-section of the concentrator sections 24 and 29. The inner annular tube 60 is the passage through which the gas flows and is adsorbed onto the wall or resin surfaces. The tube is surrounded by a space 61 through which thermal fluid flows. The outer wall 62 is insulated. Tube 26 of concentrator may have a sorbent material lining said tube. However, in some instances the target analyte may simply be collected by adsorption on the inside of tube 26.

Figure 5:
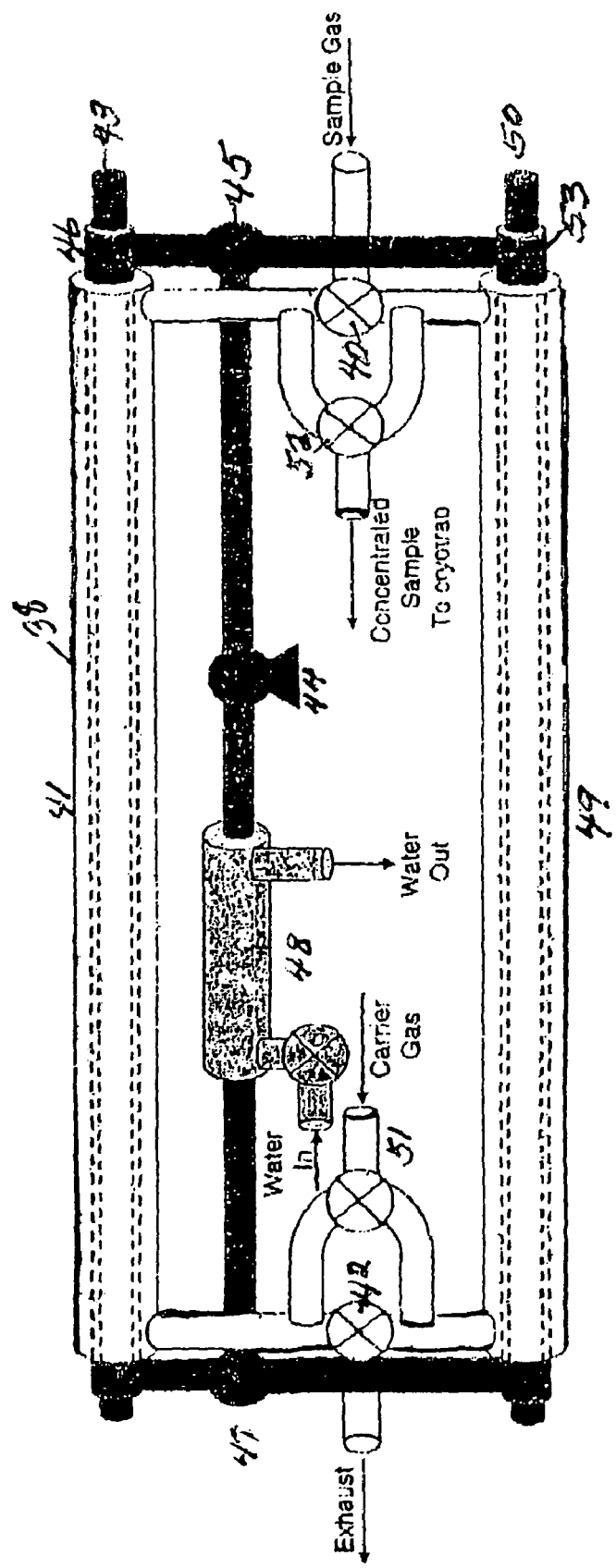
FIG. 5 is a second view of the invention showing sequenced chambers and thermal control system.

While both FIGS. 2 and 5 show concentrator systems of two chambers, one or many chambers for gas collection may be used, depending on the amount of concentration needed to analyze the target gas. It should be noted that the parameters used in description of FIGS. 2 and 5 are examples. The parameters will vary depending on such factors as the target analytes, the volume of materials to be tested and the detection means. For example, in the embodiment depicted in FIG. 2, the first concentration chamber may adsorb one low volatility target analyte while the resin-filed second concentration chamber may adsorb a second, higher volatility analyte. The carrier gas would take up both analytes and the gas finally discharged from the unit would be analyzed for both.

The concentrator presented in FIG. 2 is designed to handle an inlet sample flow rate of at least 5 L/min. During the adsorption phase, the empty tube 26 and resin-filled tube 30 are be kept at approximately 40° C. and 80° C., respectively. During the desorption phase, both inner tubes are heated to between 2500 and 300° C. and a flow of 50 mL/min of inert gas ($N_2$ or Ar) is passed through the system in the opposite direction to that of the initial sample flow. During this phase, the cryotrap 35 is maintained at a temperature of approximately −70° C. The trapped target analytes are then released from the cryotrap 35 into a flow of 1 mL/min of Ar by heating the cryotrap to 250° C. Thus, the target analytes will ultimately be concentrated from a flow of 5 L/min to 1 mL/min, a concentration factor of 5000 times. At nominal increases in the sampling time, additional increases in the concentration factor can be attained as needed. It should be noted that the flow rates and temperatures relate to the specific analytes chosen.

Figure 7:
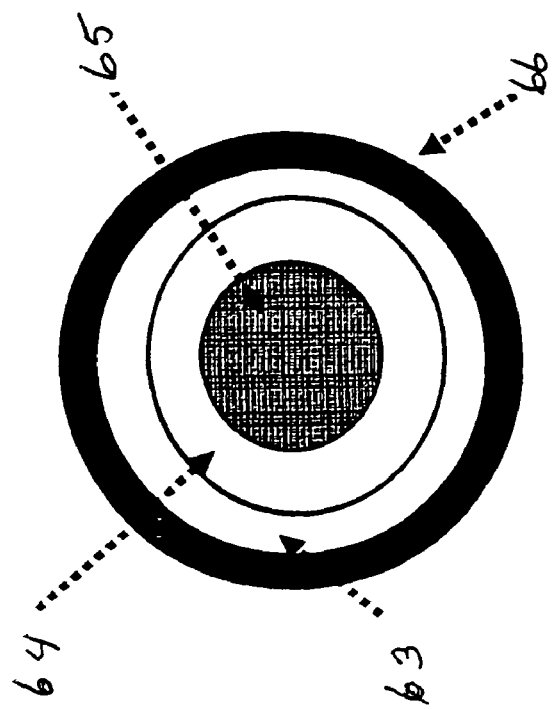
FIG. 7 shows a cross-section view of the adsorption chambers of FIG. 5.

A second embodiment of the concentrator system involving a different configuration that follows the same principles is shown in FIG. 5. The particle-free sample flow exiting the filter system enters the concentrator through the sample inlet valve 40 opened toward the sorbent resin-filled bed 41 having an outer wall 38 enclosing the bed and exits through the open exit valve 42. The bed 41 to which the sample is sent is in the adsorbing mode. During sampling (adsorbent mode) the electrical heating rod 43 contained in a tube 46, which is concentric to bed 41 is maintained in the "OFF" state. Heat transfer thermal fluid flows through a pump 44 and through a three-way valve 45 which is open to the inner tube heat exchanger 46 concentric to the adsorbing bed 41. A cross section of the bed with surrounding wall is seen at FIG. 7. The heat transfer thermal fluid returns to pump 44 after passing through three-way valve 47 and through the water-cooled heat exchanger 48. Once the temperature of the bed 41 reaches the set temperature, which is a function of the target compound type and adsorption temperature of the sample gas, the gas sample flows through open valve 40 and into resin-filled bed 41. While the target compounds from the sample are being adsorbed onto bed 41, thereby concentrating them on the resin, the parallel resin bed 49 is in a desorbing mode. In the desorbing mode, heating rod 50 is in the "ON" state to heat bed 49 to the desorption temperature (the temperature at which the target compound is desorbed). An inert gas flow enters through gas valve 51, which is open to resin-filled bed 49 and closed to adsorbing bed 41, to carry the desorbed target compounds through sample valve 52. During the desorption mode, no heat transfer thermal fluid flow moved through the inner heat exchanger 50 contained in a tube within bed 49, since valves 45 and 47 of the loop are opened to bed 41 and closed to bed 49. The concentrated sample flow exiting through valve 52 is sent to a detection means (such as on-line jet-REMPI/TOFMS) via a cryotrap focusing step. In this embodiment, the sample is sent into the sorbent bed in adsorbing mode. The bed containing the sorbent resin concentrically surrounds tubes 46 and 53 containing heat transfer thermal fluid. The central axes of tubes 46 and 53 contain electrical heating rods 43 and 50, thereby enabling the heating rod to be surrounded by the heat transfer thermal fluid.

Referring to FIG. 7, this drawing shows a cross-section of the container sections 38 and 49 of FIG. 5, there is an inner annular tube through which target gases flow 63 surrounded by an annular space 64 through which thermal fluid flows. A heating rod 65 is in the center of this adsorber unit. The outer wall 66 is insulated. The concentrating zone of FIG. 5 are configured differently from those of FIG. 2 in that they are in parallel and their sorptive surfaces are independent of each other. The zones can be sequentially sampled and analyzed for similar or different target analytes.

After the desired adsorbing time, which is determined by the required target compound concentration and the time necessary to desorb the target compound, the states of the valves 40, 42, 51, 52 and heating rods 43, 50 switch to bring bed 41 into the desorption mode and bed 49 into the adsorption mode. This design allows for continuous sampling and desorption steps. All actions of the concentrator system discussed herein are automated via a visual basic computer code allowing for users to adjust parameters such as the adsorption and desorption temperature and sampling time.

After exiting valve 25 (FIG. 2) or 52 (FIG. 5), the concentrated sample passes into a cold cryotrap (not shown in FIG. 5) to condense out the target compounds from the inert gas flow and further concentrate the target compounds. After desorption, the inert carrier gas flow is stopped. The cryotrap is then rapidly heated to vaporize the trapped target compounds which are then carried to the target compound analyzer with an inert gas flow of 1 mL/min. The particular embodiments disclosed herein were designed to handle an intake flow of 5 L/min, thereby providing a concentration increase of more than 3 orders of magnitude in the gas stream to be measured by the target compound analyzer. The actual concentration factor is a function of the instrument response and the sampling time to the target compounds.

While the cryotrap may not be needed for all applications, it is advised that its use can be very important, since when a fixed analyte mass is released in a shorter time, the signal concentration increases, making detection easier and more certain.

The resin-filled beds 29, 41 and 49 use adsorbents such as TENAX™ TA. The cryotrap is cooled to between approximately −70° and −50° C., and such cooling is accomplished via the use of a cryogenic heat transfer thermal fluid such as Dynalene™, which is used as the heat transfer thermal fluid for the cooling process in beds 24, 29, 41 and 49. The subsequent selected hot desorption temperature of the cryotrap used during the vaporization phase is a function of the target compound's vaporization properties and the rate of heating. For example, a temperature of 300° C. and a time of 10 to 15 minutes are required for some halogenated aromatics. This temperature may be achieved with an electric heating element. Inert analyzer carrier gases such as Argon (Ar) and nitrogen ($N_2$) are used as the inert concentrator carrier gas.

If a substantial quantity of the target analytes is present on particles and is desired to be quantified, a heater surrounding filter 2-9 in FIG. 1 can be raised to temperatures higher than the filter heater 10 causing removal by vaporization of the target organic species on the particles, provided that the target analyte is not chemically altered by the heat. These vapor species are then sent to the concentrator in FIG. 2 via system outlet 18.

While the figures herein disclose two sorbent beds, this is a suggestion. More beds could be used to either increase efficacy of the system in concentrating a given analyte or for concentrating more than one analyte if sorbent beds with different adsorption qualities are used. In some instances, only one sorbent bed may be sufficient to provide needed concentration. It would also be possible to have multiple beds sorbing simultaneously rather than sequentially to concentrate different analytes.

Figure 3:
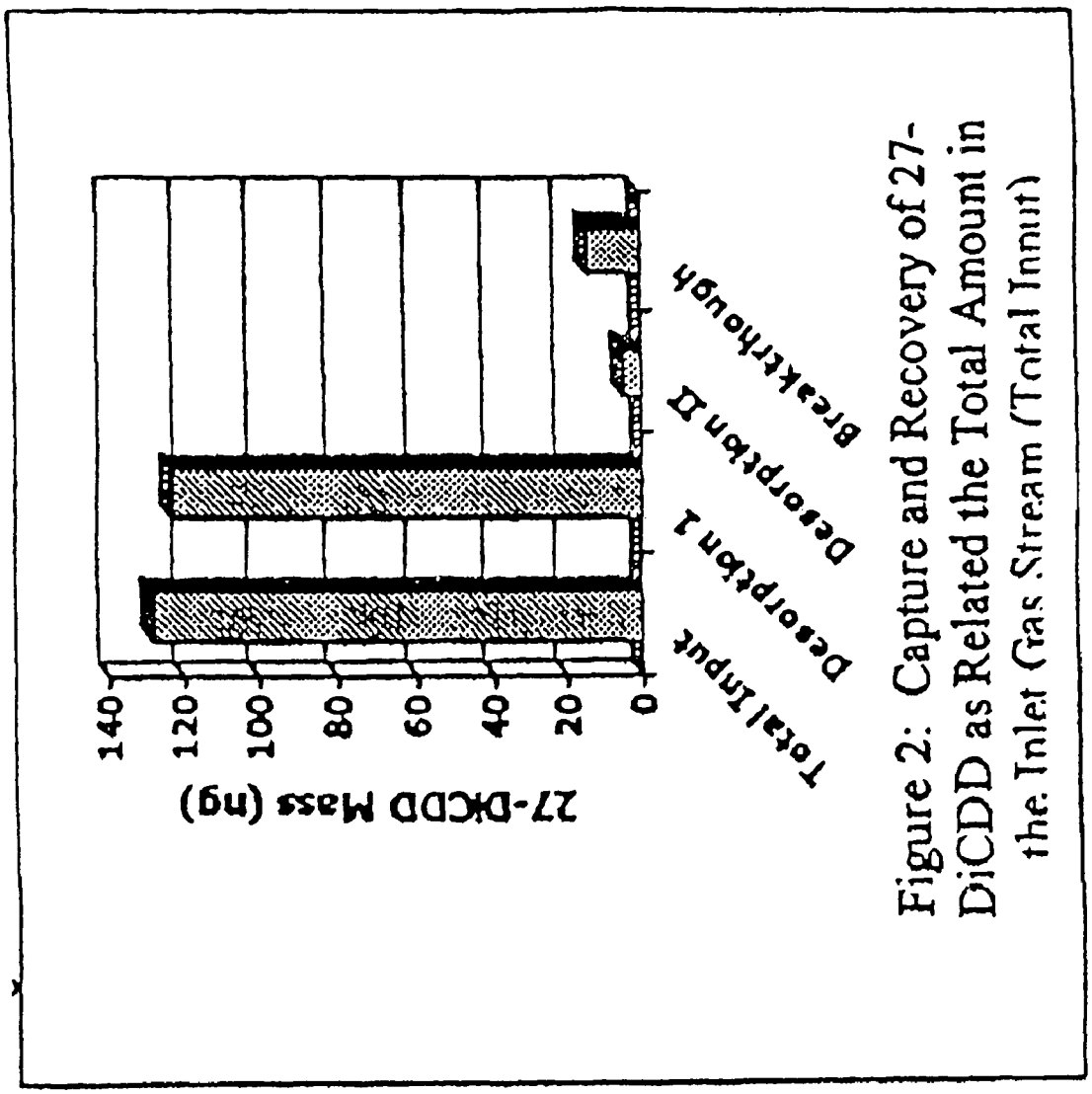
FIG. 3 shows extent of recovery of an analyte gas from a stream.

Results:

To test the capture of the target PCDD/F (polychlorinated dibenzodioxin/dibenzo furan) compounds from a combustion process flue gas, a 70 ppt concentration of 2,7-dichlorinated dibenzo-p-dioxin (27-DiCDD) in nitrogen was passed through a 6 inch bed of TENAXT™ held at 80° C. This concentration is below the real-time detection limit of the jet-REMPI instrument for this particular target compound. After the 5 L/min flow was passed through the bed ("total input" FIG. 3), it was bubbled through toluene to trap any 27-DiCDD that broke through the bed. After 30 minutes, the flow was switched to pure nitrogen (100 mL/min) and the toluene trap was replaced by a fresh toluene trap. The bed was heated to 250° C. for 30 minutes to assess the desorption of the target compound from the TENAX™ (desorption I). This desorption step was repeated again at 1 L/min for an additional 30 minutes to determine if additional time or higher flow rate would be needed to recover all of the trapped PCDD/F (desorption II). As presented graphically (FIG. 3), greater than 90% of the 27-DiCDD was captured by the sorbent bed and more than 98% was desorbed during the first desorption step. The minimal amount of breakthrough and loss (without the second desorption step) suggested that the two six inch TENAX™ beds in the current concentrator design would be sufficient to trap the target PCDD/F compounds present at low concentrations in the inlet gas flow. A temperature of 80° C. was used in the test to assure that a temperature high enough to prevent condensation of water in the flue gas was maintained in the concentrator system. The successful results at this temperature simplify the system by removing the need to deal with the moisture in the flue gas.

Figure 4:
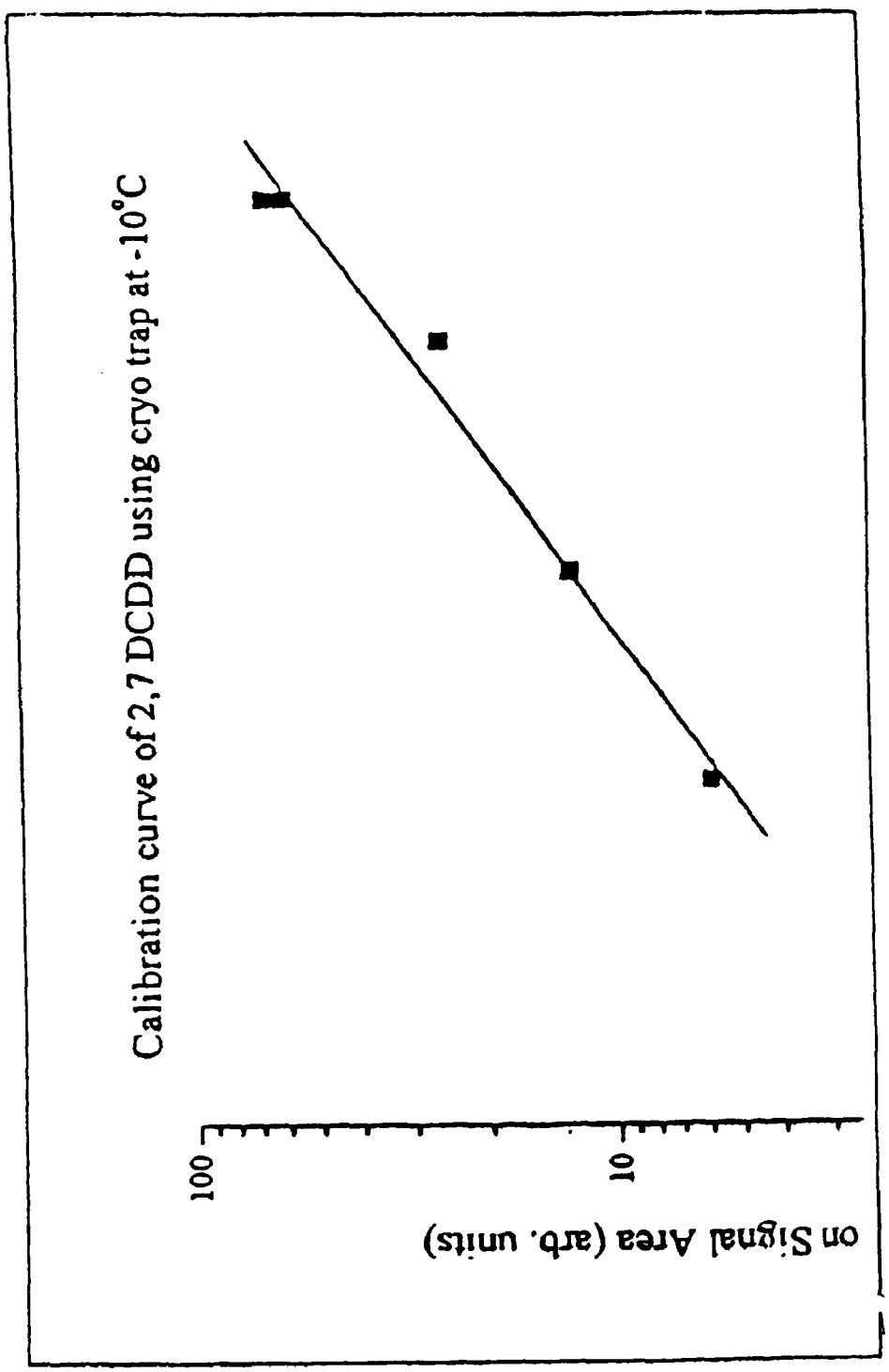
FIG. 4 is a graph of a calibration curve of integrated area to total target compound amount.

To test this interface, a flow of 50 mL/min nitrogen containing selected concentrations of 27 DiCDD was passed through a 0.51 mm I.D. capillary tubing cooled to −10° C. by the cryotrap. After 5 minutes the flow was switched to a 1 mL/min pure Ar flow and the cryotrap was heated to 250-300° C. The 27-DiCDD signal in this flow was monitored via the jet-REMPI instrument. The 1 mL/min flow was used to match the inlet flow of the jet-REMPI instrument to ensure that all of the target compound trapped in the cryotrap was sampled. The total amount (ng) of the target compound trapped in the cryotrap could be correlated to the area under the signal monitored by the jet-REMPI instrument. By changing the inlet 27-DiCDD concentration during the trapping step, a calibration curve of integrated area to total target compound amount was generated (FIG. 4). The lowest amount of 27-DiCDD detected was 4.4 ng which had a signal to noise ratio of 6. By increasing the gain, a detection limit of 330 pg was estimated at a signal to noise ratio of 3. Since the current concentrator design was tested at 5 L/min, a flue gas would have to have a concentration of 13.2 ng/dscm (1.3 pptv) to be detectable by the concentrator/jet-REMPI system after a 5 minute concentration. Obviously, an inverse relationship between the concentration time and flue gas concentration holds. For example, a sampling time of just 15 minutes requires the flue gas to have a target compound concentration of around 450 ppqv or higher in order to be measured. For comparison, the real-time detection limit for 27-DiCDD via the jet-REMPI instrument has been estimated as 240 pptv based on extrapolation of the lowest detectable signal with a signal to noise ratio of 3 adjusted for the increase in gain that could be achieved.

In view of the above, it is clear that the concentrator system of the invention that can be directly integrated with the jet-REMPI instrument will allow for near real-time measurements of target compounds with concentrations in the ppqv range, thus providing considerable advantage over prior art systems. The resulting improvement in detection using a 5 minute sampling time increases efficacy by almost 200 times that of comparative systems. Detection is inversely related to the sampling time, thus, doubling the sampling time results in a two times reduction in the detectable concentration.

What we claim is:

1. An apparatus comprising:
a revolving filter tray system and a concentrator system;
said filter tray system comprises: (a) a motorized rotatable tray, said tray having multiple filter holders including filters, each said holder having a sample inlet and a sample outlet; (b) an inlet sample line; and (c) an outlet sample line, wherein said tray is configured to rotate and position one of said holder including said filter such that said inlet sample line engages said sample inlet of one of said multiple holders, and said outlet sample line engages said sample outlet of one of said multiple holders;
said concentrator system having a gas/vapor passage having an entrance and an exit port, said concentrator system having at least one gas/vapor inlet connected to said entrance port of said gas/vapor passage, said passage comprises at least one sorbent bed, each said sorbent bed encompassed by a concentric passage, said concentric passage having an inlet and an outlet port, said exit port of said concentrator system leads to a cryotrap; and
wherein said outlet sample line of said filter tray system leads to said at least one gas/vapor inlet of said concentrator system.

2. An apparatus comprising:
a revolving filter tray system and a concentrator system;
said filter tray system comprises: (a) a motorized rotatable tray, said tray having multiple filter holders including filters, each said holder having a sample inlet and a sample outlet; (b) an inlet sample line; and (c) an outlet sample line, wherein said tray is configured to rotate and position one of said holder including said filter such that said inlet sample line engages said sample inlet of one of said multiple holders, and said outlet sample line engages said sample outlet of one of said multiple holders;

said concentrator system having a gas/vapor passage having an entrance and an exit port, said concentrator system having at least one gas/vapor inlet connected to said entrance port of said gas/vapor passage, said passage comprises at least one sorbent bed defining concentric passage, said sorbent bed being concentric with a heat source, said exit port of said concentrator system leads to a cryotrap;

wherein said outlet sample line of said filter tray system leads to said at least one gas/vapor inlet of said concentrator system.

3. The apparatus of claim 1 wherein there is a series of at least two gas/vapor passages having said sorbent beds which are in serial arrangement.

4. The apparatus of claim 1 wherein said at least one sorbent bed contains resin particles.

5. The apparatus of claim 1 wherein there is, in series, at least two gas/vapor passages having said sorbent beds in parallel arrangement.

6. The apparatus of claim 5 wherein said at least one sorbent bed contains resin particles.

7. The apparatus of claim 1 wherein the walls of said gas/vapor passages are wrapped with resistive heating elements.

8. The apparatus of claim 2 wherein there is a series of at least two gas/vapor passages having said sorbent beds in parallel arrangement.

9. The apparatus of claim 8 wherein said at least one sorbent bed contains resin particles.

10. The apparatus of claim 2 wherein the walls of said gas/vapor passages are wrapped with resistive heating elements.

11. The apparatus of claim 1 further comprising a temperature controlled housing, wherein said revolving filter tray system is enclosed in said temperature controlled housing.

12. The apparatus of claim 2 further comprising a temperature controlled housing, wherein said revolving filter tray system is enclosed in said temperature controlled housing.

* * * * *